(12) United States Patent
Gittleman

(10) Patent No.: US 6,913,461 B2
(45) Date of Patent: Jul. 5, 2005

(54) TRIPLE TRAY WITH FLEXIBLE JOINT

(76) Inventor: Neal B. Gittleman, 50 Briar Hollow La., Suite 150 West, Houston, TX (US) 77027

(*) Notice: Subject to any disclaimer, the term of this patent is extended or adjusted under 35 U.S.C. 154(b) by 42 days.

(21) Appl. No.: 10/696,351

(22) Filed: Oct. 29, 2003

(65) Prior Publication Data
US 2005/0095553 A1 May 5, 2005

(51) Int. Cl.[7] .............................................. A61C 9/00
(52) U.S. Cl. ........................................ 433/38; 433/37
(58) Field of Search ............................ 433/37, 38, 41, 433/42, 43, 45, 47, 48, 34, 36, 29, 229

(56) References Cited

U.S. PATENT DOCUMENTS

| | | | |
|---|---|---|---|
| 5,316,473 A | * | 5/1994 | Hare ............................ 433/29 |
| 5,702,250 A | * | 12/1997 | Kipke ........................... 433/37 |
| 6,450,808 B1 | * | 9/2002 | Pelerin .......................... 433/38 |
| 2003/0044748 A1 | * | 3/2003 | Tucker et al. .................. 433/38 |

* cited by examiner

*Primary Examiner*—Melba Bumgarner

(57) ABSTRACT

An apparatus and method to avoid dental impression material distortion comprised of dental impression triple tray with a flexible hinge rendered inflexible by a light-cured compound. The curing light is conveyed by an optical fiber assembly. Accurate simultaneous impressions of upper and lower impressions and bite registration, with the mouth completely closed and the jaw accurately positioned in centric closure are insured. Spring back of the impression tray frame caused by bite pressure against points on the frame are minimized by allowing the hinge element to initially flex when first placed in the mouth. While the impression polymer is curing, a light of the proper frequency range is delivered via the optical fiber to the light-cured compound in the hinge area to render the hinge inflexible.

8 Claims, 5 Drawing Sheets

Figure 1:
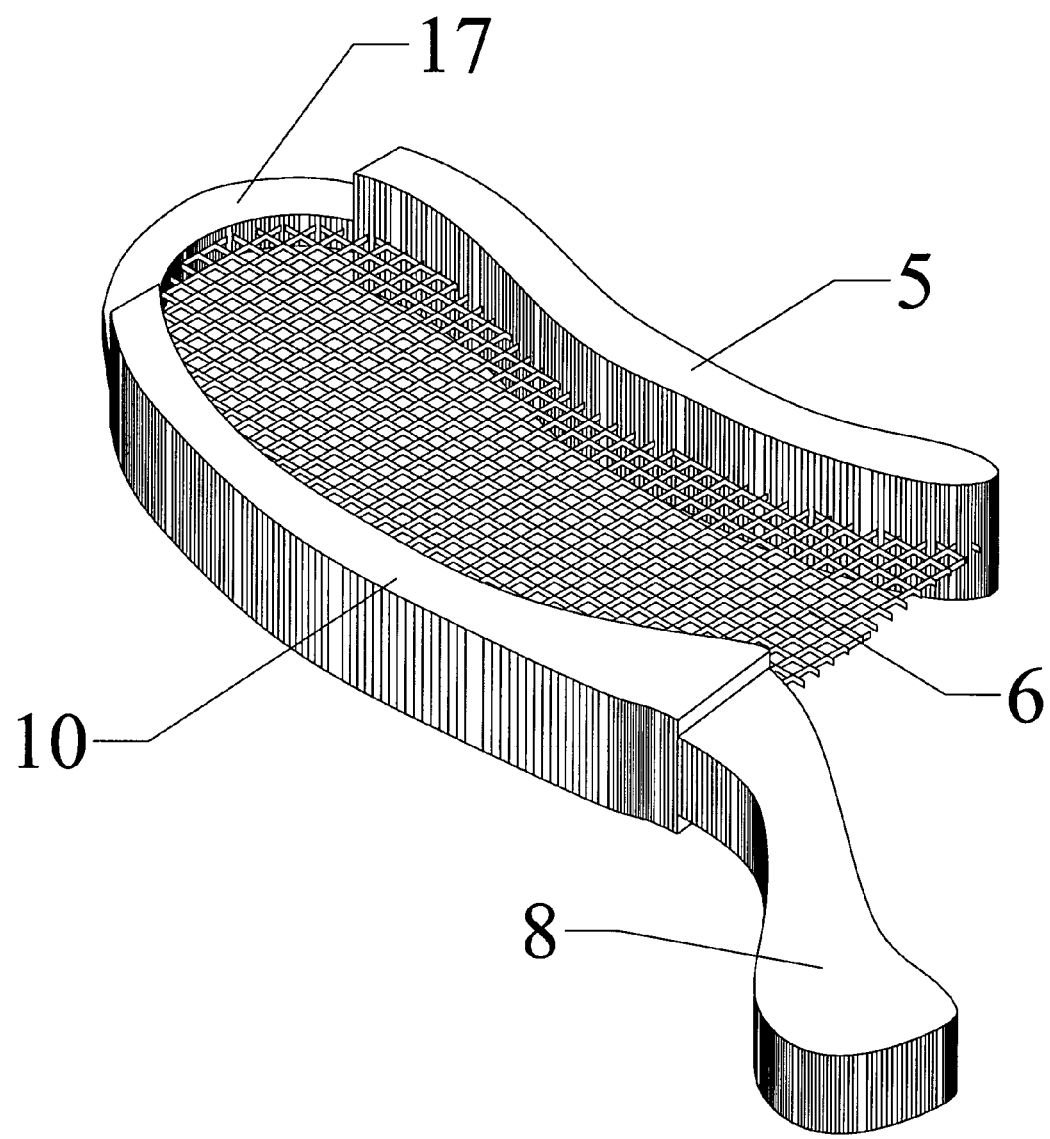

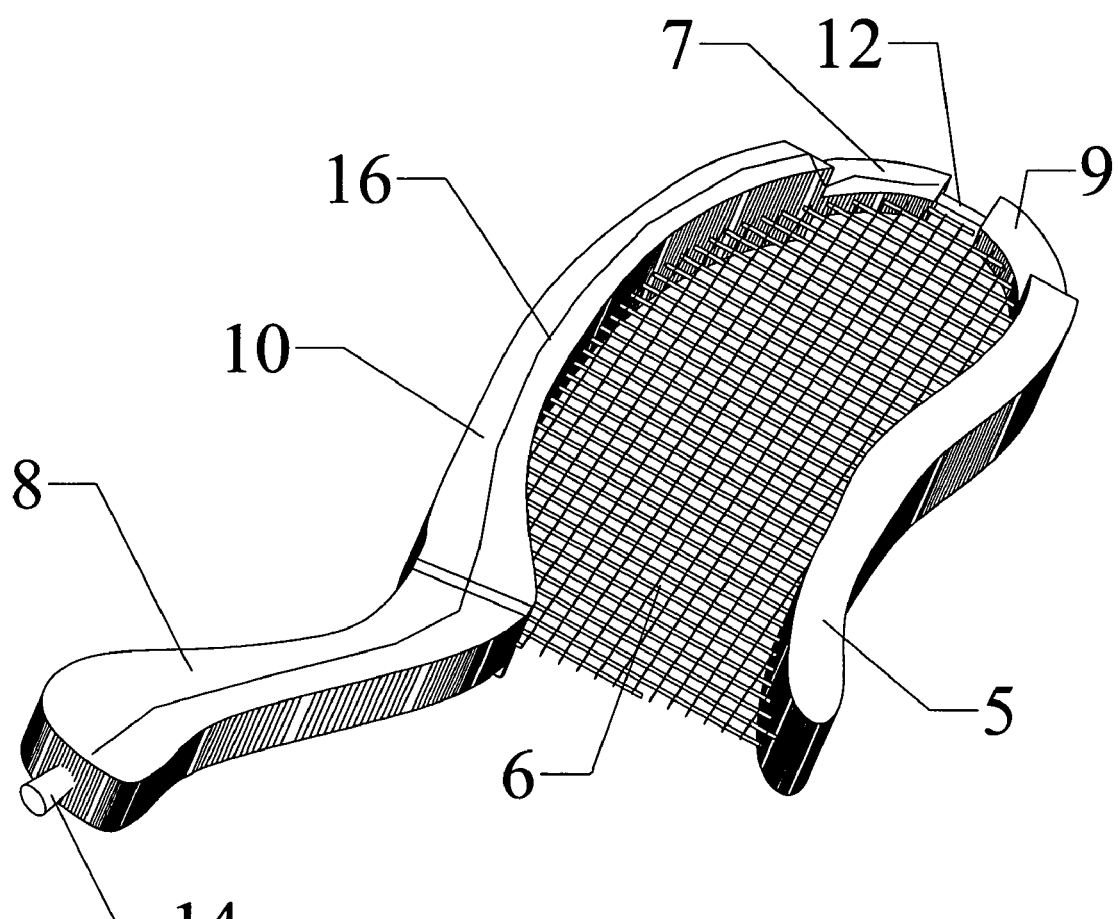
Figure 2_A

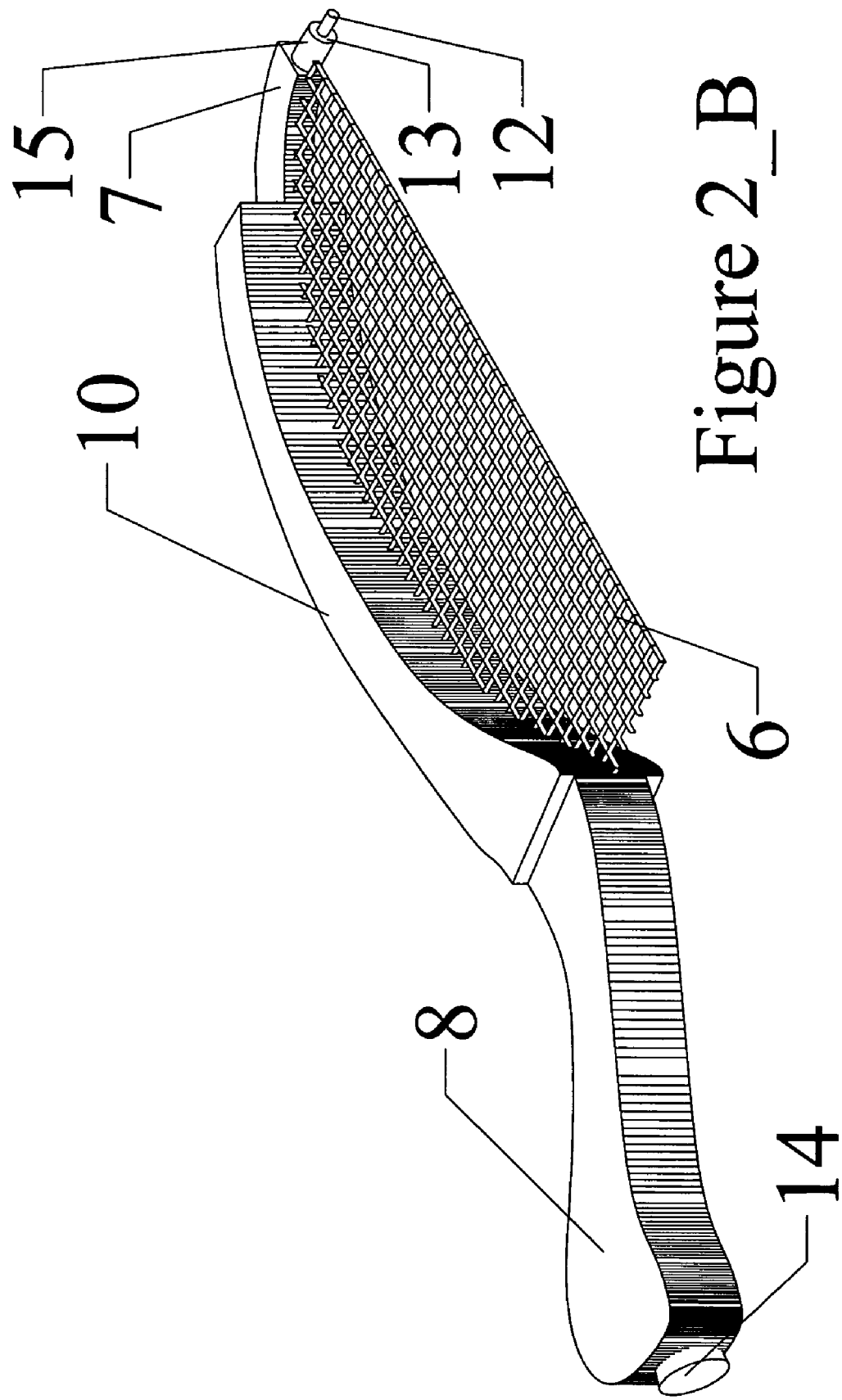
Figure 2_B

TRIPLE TRAY WITH FLEXIBLE JOINT

BACKGROUND OF THE INVENTION

In the field of dentistry, patient comfort and the efficient use of a dentist's time are paramount. Likewise, precision alignment of prosthetic components is essential. The need to match both natural and artificial, upper and lower teeth to within 5 microns and provide accurate mating of the prosthesis with existing teeth requires accurate replication of oral structures when making dental impressions. To create these accurate models and the final prosthesis, a matched upper and lower impression can be obtained simultaneously with the jaw in the closed position and the teeth in the interdigitated position (centric occlusion). A triple tray is used to simultaneously register the upper and lower bite while making simultaneous upper and lower impressions of dental and soft tissue structures. Most triple trays currently on the market are molded as a single piece from thermoplastic compound. This plastic may be stressed or distorted during the taking of the impression by the bite pressure and has the tendency to exert a distorting pressure on the flexible impression material after the triple tray is removed from the mouth. This misshapen impression material will result in an ill-fitting prosthesis. The present invention remedies this oversight.

As an example of conventional existing practice, the following procedures are performed when preparing an implant prosthesis. After dental implants have healed into the underlying bone structures of the mandible or maxilla and the soft gum tissue has healed, a full set of upper and lower impressions of the mouth are made using individual full or partial arch upper and lower trays. Positive casts of these impressions are mounted upon a mechanical articulator that mimics the motion of the temporo-mandibular joint (tmj). A separate bite registration cast is also made. These positive casts are equipped with accurately placed implant fixture analogs positioned to accurately replicate the structures in the mouth. These positive casts are tested against the bite registration cast.

In the conventional procedure, the healing caps are removed from one or more dental implant fixtures and impression transfer posts are accurately attached to each implant fixture. An impression tray filled with a self-hardening elastomeric impression material is pressed over the region of the dental arch containing the impression transfer posts.

After a few minutes, the elastomeric impression material has set and the impression is removed with a gentle parting pressure. The impression transfer post snaps from its positive detent within the impression material. Then the impression transfer post is unscrewed from the implant and attached to an implant analog with the screw. The healing cap replaced on the dental implant. Now the analog of the dental implant is accurately attached to the impression transfer post that was snapped back into the elastomeric impression material. The same procedure is followed for the opposing dental arch. A third, bite registration impression is taken without the impression transfer posts installed and the teeth in centric closure.

A stone model of the mouth structure with the dental implant analog exactly aligned and retained is created from the separate impressions. These models are combined upon an articulator mimic the actual jaw motions. A model of the final prosthesis is built up and tried in for a non-interfering, good fit. This model relying upon properly placed dental implant analogs cast in the properly aligned position is used to build the final prosthesis.

In the improved procedure, in order quickly to make an accurate, simultaneous impression of the upper and lower teeth in the correct alignment, the practitioner uses a 'triple tray.' This tray consists of a molded plastic assembly with a handle connected to a set of confining dams and a thin open screen mesh. The mesh is oriented horizontally and is to be placed between the mating occlusal surfaces of the teeth while the jaw is in the closed or centric position. The buccal and lingual dams of the frame are molded to the mesh. A paste of quick-setting elastomer is placed on both sides of the mesh within the confines of the dams. The mouth is closed with the upper and lower teeth in the closed or centric position while imbedded within the curing elastomer. In this manner, a matching set of aligned upper and lower impressions along with the proper bite registration are made.

The elastomeric impression materials, such as polyvinylsiloxane or polyether, are dimensionally stable, but are flexible to allow removal from the teeth and the stone replicas. If the triple tray was distorted during the taking of the impression, the replica will not be true. Likewise, the impression transfer post position cannot be ensured and thus accurate replication of the implant within the models mounted upon the articulator will be compromised. If low profile impression transfer posts in combination with the triple tray are used, accurate registry of the elastomeric impression to the dental implant analog occurs. Instead of taking three time-consuming, separate impressions of the upper arch, lower arch and bite registration, a single impression is formed, thus, the 'triple tray' name. If a single area of the partially edentulous mouth is being modeled, a half-arch, triple tray can be used.

The preferred embodiment of this invention has at least two stiff, molded portions of the triple tray frame bridged by a flexible optical fiber assembly acting as a stress relieving member or hinge. The two portions of the frame are discontinuous except for the horizontal mesh and the flexible fiber assembly. The frame elements are dissected in this fashion. When the impression is taken, the fiber first bends to allow the rigid frame sections to accommodate the displacing forces from surrounding tissues. While the impression polymer is curing, a beam of light of the proper frequencies is transmitted along the optical fiber to the region of the flexible bridge and cures an optical compound surround the bridging fiber to limit its flexibility and secure the frame portions as one rigid piece. Several bridging regions are anticipated by this invention for triple trays incorporating the anterior region of the mouth.

A BRIEF DESCRIPTION OF THE DRAWINGS

Figure 3:
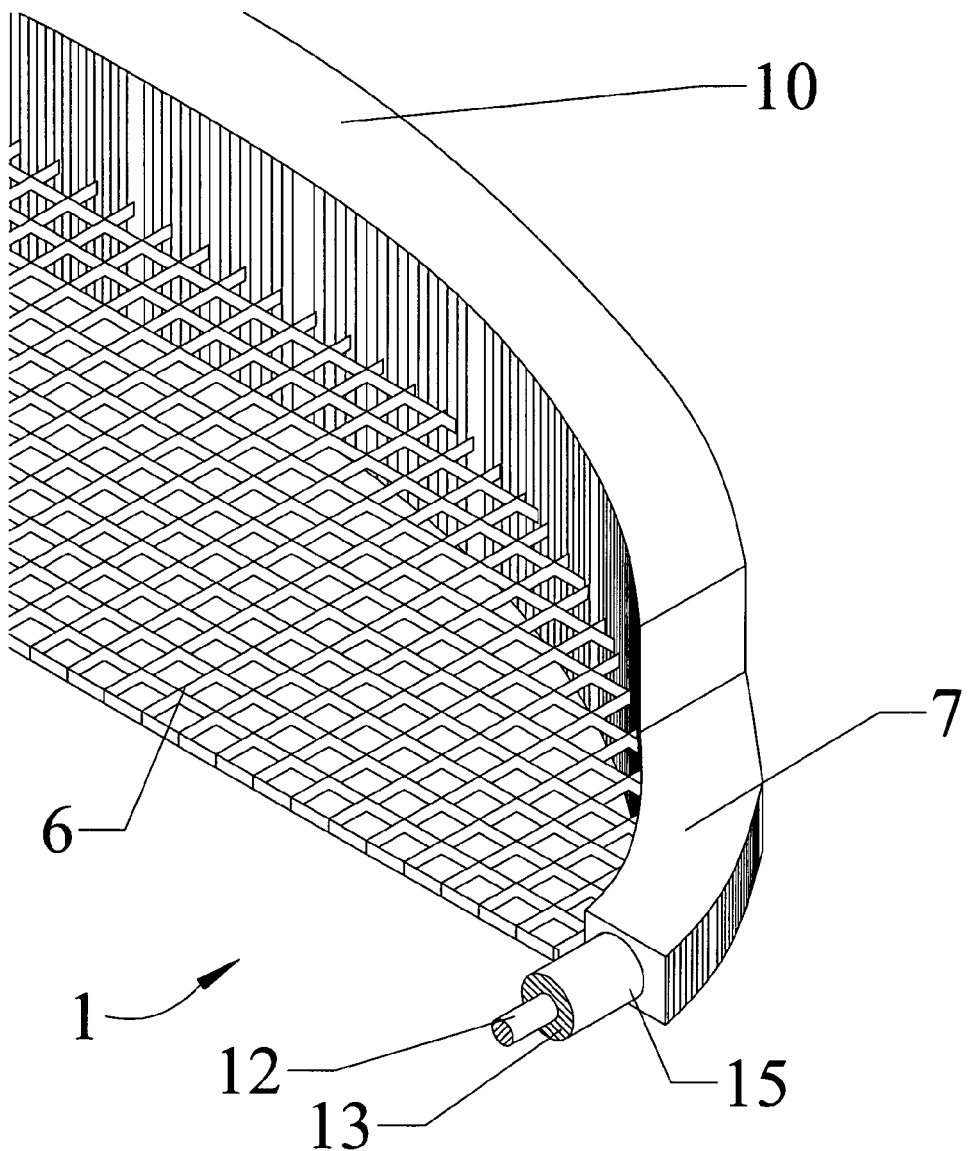

FIG. 1 (prior art) details a perspective view of an anterior triple tray;

FIGS. 2_A and 2_B shows a perspective view of a triple tray with included optical fiber assembly;

FIG. 3 is a closer perspective cross-section of the optical fiber hinge; and

Figure 4:
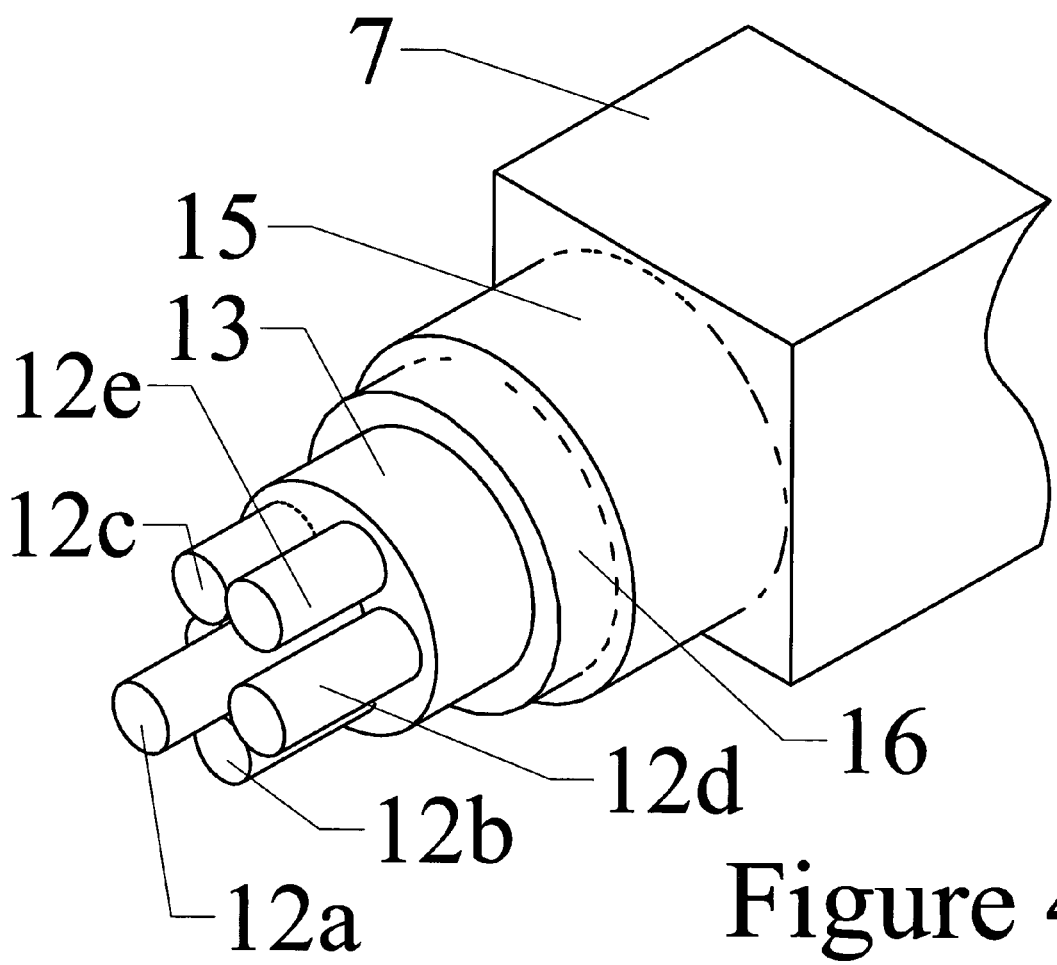

FIG. 4 details a cross section of a multiple optical fiber bundle.

A DETAILED DESCRIPTION OF THE DRAWINGS

A fairly accurate model can be simultaneously fabricated from an impression of the upper and lower jaws with remaining natural teeth and dental implants by means of a triple tray. FIG. 1 (prior art) shows a typical molded plastic anterior triple tray with handle 8, curved outer buccal dam wall 10, curved inner lingual dam wall 5 and horizontal open mesh 6. Transition region 17 is a thinned but rigid curved frame member that holds both dam walls in place. Region 17 is modified in this invention to improve the art. A quick setting polymer paste is placed in an arc on both upper and lower sides of the mesh. The dentist places the triple tray in the patient's mouth and closes the jaw in a natural occluded, centric position. The thin loose mesh 6 conforms to the touching occlusal surfaces of the upper and lower teeth while the polymer completely enfolds the teeth, implants and other oral structures to form an accurate impression. However, pressures at points on the triple tray frame caused by portions of the oral anatomy can deform the triple tray resulting in a less than accurate impression.

FIGS. 2_A and 2_B embody the preferred improvements in triple tray design by including a flexible hinge 12 formed in part by the distal end of an optical fiber assembly that bridges triple tray frame members 7 and 9. The optical fiber assembly is hidden within the frame approximately along pathway 16. The proximal end 14 of the optical fiber emerges from the handle 8 in a convenient place. The proximal end can be of a diameter to match the typical curing lamp used by dentists and can consist of a molded clear conic "light funnel" to direct the curing light into the smaller diameter optical fiber assembly. During the time the polymer is setting up, a UV/blue light is directed in optical fiber proximal end 14 to harden the light cured epoxy compound 13 at the distal end of the fiber 12. The frame members 7 and 9 are now firmly joined at a proper angle without stressing the polymer impression compound. A number of UV or blue light-curing compounds are available from Loctite™ and other manufacturers. These are light sensitive polymethacrylates or acrylics under current manufacture, but the invention anticipates other formulations performing the same function to be applicable. These light-cured polymers are available in a variety of viscosities and wetting properties to adhere to the frame members 7 and 9 while remaining in place around the distal end of optical fiber 12 within flexible tube 15. The optical fiber 12 can be made from acrylic or glass in single or multiple strands of a diameter to provide both initial flexibility and final rigidity. Acrylic fibers transmit blue light to effectively set the light-cured polymer within a minute or less using the commonly available UV/blue curing lamps used by dentists to harden composite compounds. The distal end of optical fiber 12 can be treated to surrender the majority of its light into the surrounding light-cured polymer. The treatment can be a series of stipules or lens-like deformations pressed into the distal end of the plastic optical fiber much as a cylinder of metal is coined or knurled by a knurling tool. Frosting or roughening to create many small scratches to disperse the light in multiple directions by lightly sanding, sand blasting or chemically treating the distal end of the fiber will accomplish the same task. If the light cured, viscous polymer has a refractive index similar to the optical fiber, the light will easily spread from the distal end of the optical fiber without any pretreatment of the fiber end. The surrounding flexible coaxial tube 15 should have a white reflective interior to reflect and distribute the UV/blue light throughout the polymer for a full optical cure.

FIG. 3 shows closer perspective view of the cross section through the optical fiber assembly with an optical fiber 12 is surrounded by a viscous, ultraviolet (UV) or blue light-hardened, compound 13 contained within a coaxial flexible tube 15. This flexible tube can be an extruded, opaque, internally white rubber material such as vinyl or other soft polymer and stretched over a hollow projection or forced into countersunk holes on frame elements 7 and 9 to effectively contain the viscous liquid light-cured polymer.

FIG. 4 details a multiple optical fiber hinge assembly. As an example, the optical fiber assembly can consist of several optical fibers 12a, 12b, 12c, 12d and 12e in a parallel bundle. These fibers can be allowed to slip past each other to improve flexibility. The light-cured polymer 13 fills the spaces between the fibers. When hardened by light the group of fibers are adhered to each other and thereby stiffened. An opaque flexible jacket or tube 16 of vinyl or other material contains the viscous, light-cured polymer. An annular boss or nipple 15 connects the flexible jacket to frame members 7 and 9 to form a liquid tight seal to contain the light-cured polymer 13.

In a similar fashion, a mixture of small clear spheres of plastic or glass and the light-cured polymer can surround a single fiber. The small glass or plastic spheres act to both disperse the curing light and to structurally stiffen the cured compound around the central fiber. Transparent particles with multiple facets can be used to disperse the light throughout the polymer compound.

The triple tray frame has a channel to accommodate the optical fiber assembly. The triple tray frame can be molded around the optical fiber assembly at the time of molding. Alternately, the optical fiber assembly can be inserted into a molded groove after the molding is completed. This groove can be molded with detents to retain the fiber assembly in place.

What is claimed is:

1. A dental implant registration apparatus comprising:
   an impression tray having
   a curved dissected frame;
   a horizontal mesh;
   a light conveying fiber assembly having a flexible distal end;
   a light curable compound surrounding said flexible distal end;
   a flexible coaxial tube containing said light curable compound and
   said flexible distal end of said light conveying fiber assembly; and
   a proximal end of said light conveying fiber assembly having a light entry port;
   said flexible distal end of said light conveying fiber assembly rendered inflexible by the hardening of said light curable compound upon entry of curing light into said light entry port.

2. An apparatus as cited in claim 1 comprising said fiber assembly having a single optical fiber.

3. An apparatus as cited in claim 1 comprising said fiber assembly having several said optical fibers.

4. An apparatus as cited in claim 1 comprising said flexible distal end treated to disperse said curing light throughout said light curable compound.

5. An apparatus as cited in claim 1 comprising transparent particles surrounding said flexible distal end and said transparent particles embedded in said light curable compound to disperse said curing light throughout said light curing compound.

6. An apparatus as cited in claim 1 comprising transparent spheres surrounding said flexible distal end and said transparent spheres embedded in said light curable compound to disperse said curing light throughout said light curing compound.

7. An apparatus as cited in claim 1 having said curved dissected frame comprising several dissected sections.

8. An apparatus as cited in claim 1 comprising said proximal end of said light conveying fiber assembly having a transparent, conic light funnel to direct said curing light into said light conveying fiber assembly.

* * * * *